United States Patent [19]

Liu et al.

[11] Patent Number: 4,954,582
[45] Date of Patent: Sep. 4, 1990

[54] BENZYLOXY VINYL ETHERS

[75] Inventors: Kou-Chang Liu, Wayne; Paul D. Taylor, West Milford, both of N.J.

[73] Assignee: GAF Chemicals Corporation, Wayne, N.J.

[21] Appl. No.: 404,468

[22] Filed: Sep. 8, 1989

[51] Int. Cl.$^5$ .......................... C08F 16/26; C08G 8/30
[52] U.S. Cl. ..................................... 525/502; 568/609; 568/640
[58] Field of Search ................ 525/502; 568/609, 640

[56] References Cited

U.S. PATENT DOCUMENTS

| 3,248,276 | 4/1966 | Bean et al. | 525/502 X |
| 3,800,004 | 3/1974 | Sherwood et al. | 525/502 |
| 4,159,285 | 6/1979 | Passalenti et al. | 525/502 |
| 4,755,569 | 7/1988 | Kanagawa et al. | 525/502 |

Primary Examiner—Earl Nielsen
Attorney, Agent, or Firm—Marilyn J. Maue; Joshua J. Ward

[57] ABSTRACT

The invention relates to benzyloxy vinyl ethers having the structure

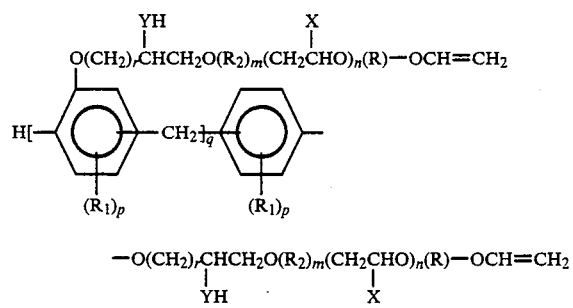

wherein
$R_1$ is lower alkyl;
p is an integer having a value of from 0 to 2;
q is an integer having a value of from 1 to 20;
r is an integer having a value of from 1 to 6;
n is an integer having a value of from 0 to 20;
m is an integer having a value of from 0 to 1;
Y is sulfur or oxygen;
X is hydrogen or methyl and
R and $R_2$ are each independently a radical having from 2 to 20 carbon atoms and are selected from the group of alkylene, arylene, aralkenylene and alkarylene optionally substituted with lower alkyl.

The invention also relates to the process for preparing the above multifunctional benzyloxy vinyl ethers.

7 Claims, No Drawings

BENZYLOXY VINYL ETHERS

In one aspect this invention relates to novel, polyfunctional benzyloxy vinyl ethers and the process for their preparation. In another aspect the invention relates to oligomeric materials which are rapidly curable in the presence of air or oxygen by irradiation to strongly adhesive and chemically resistant coatings. In still another aspect the invention relates to polyfunctional resins which are suitable as adhesives, inks or chemical intermediates.

BACKGROUND OF THE INVENTION

The demand for radiation curable coatings, adhesives and inks has rapidly increased in recent years. In general, oligomers account for more than 50% of the formulated curable raw materials by reason of their superior compatibility with many solvents and adjuvants commonly employed in coating formulations and their ease of application to substrates. Of the oligomers, acrylates which undergo radical initiated polymerization are most commonly used. However, since radical initiated processes are known to be inhibited by the presence of oxygen, care must be taken to provide an oxygen-free environment, e.g. with a blanket of nitrogen, during curing which adds to the expense of the operation. Also, it has been found that acrylate cured coatings lack the degree of adhesion and mechanical properties required in many commercial applications.

Certain epoxides have been used in some degree as oligomers for irradiation curing; however, the curing rates of these chemicals, which is exceedingly slow, has limited their use.

Accordingly, it is an object of this invention to provide a radiation curable coating material which overcomes the difficulties enumerated above.

Another object of this invention is to provide a polyfunctional resin as a coating material which is highly resistant to chemical attack, has good adhesion to substrates such as metal and glass surfaces and which are resistant to mechanical abrasion.

Another object is to provide a commercially feasible and economical process for the preparation of the present coating materials.

These and other objects of the invention will become apparent from the following description and disclosure.

THE INVENTION

In accordance with this invention there is provided a benzyloxy vinyl ether having the formula:

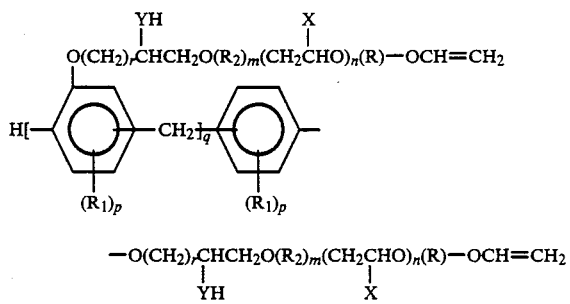

wherein
 $R_1$ is lower alkyl;
 p is an integer having a value of from 0 to 2;
 q is an integer having a value of from 2 to 20;
 r is an integer having a value of from 1 to 6;
 n is an integer having a value of from 0 to 20;
 m is an integer having a value of from 0 to 1;
 Y is sulfur or oxygen;
 X is hydrogen or methyl and
 R and $R_2$ are each independently a radical having from 2 to 20 carbon atoms and are selected from the group of alkylene, arylene, aralkenylene and alkarylene optionally substituted with lower alkyl or lower alkenyl.

The preferred benzyloxy vinyl ethers of this invention are those wherein n has a value of from 0 to 5; Y is oxygen; q has a value of from 1 to 5 and r has a value The present compounds are prepared by a simple and commercially feasible process which involves the reaction of a hydroxy vinyl ether reactant and an oxirane or thirane resin coreactant as illustrated by the equation:

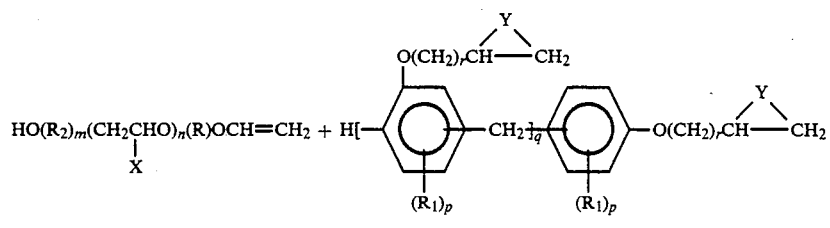

REACTANT                    COREACTANT

-continued

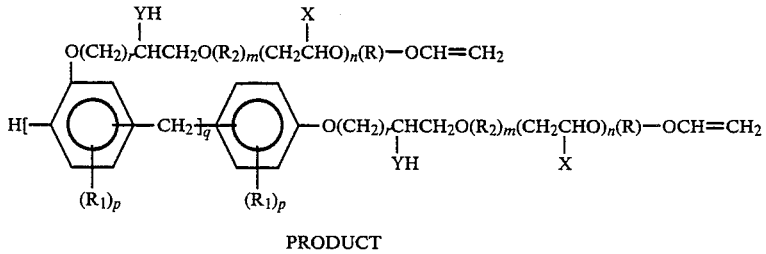

PRODUCT

The above reaction is effected in the liquid phase in the presence of a base catalyst such as potassium or sodium metal, potassium or sodium hydroxide, hydride or lower alkyl oxide or an alkaline earth metal hydroxide or alkoxide; the metal hydroxide catalysts being preferred. The catalyst is employed in a concentration of between about 0.01 and about 10 wt. %, preferably between about 0.1 and about 2 wt. % based on the coreactant.

Since the hydroxy vinyl ether reactant additionally serves as a solvent for the resin, the reaction can be carried out in the absence of extraneous diluents. However, in cases where a highly viscous resin is employed, it may be desirable to further dilute the reaction mixture with an inert solvent such as xylene, toluene, dimethylformamide and the like or a high excess of the hydroxy vinyl ether reactant which has a boiling point below that of the reaction product.

The reaction is effected at a temperature of between about 100° and about 200° C. over a period of from about 0.5 to about 100 hours, preferably at a temperature of between about 120° and about 175° C. over a period of from about 3 to 50 hours with constant agitation under a blanket of inert gas such as nitrogen, argon, and the like. The ratio of reactants is based on hydroxy groups per oxirane or thiirane moiety and can vary between about 1:1 and about 20:1, preferably from a slight excess up to 5:1 excess —OH group.

The products of the process are useful as adhesives and as highly solvent resistant, abrasive resistant coating materials which undergo substantially instantaneous curing by irradiation to provide clear, substantially colorless, flexible films when applied to a substrate. The curing process can be effected in the presence of air without the expense of maintaining an oxygen free system as was formerly needed with acrylic systems. The curing process is accomplished using any conventional technique at temperatures ranging from about 5° F. to about 110° C., preferably at ambient temperature. A major advantage of the present compounds is that they are curable at extremely high speeds, e.g. from about 700 to about 1,000 ft/minute, by exposure to a source of radiation such as UV light, electron beam and the like. The present resins are also curable by thermal or radical initiated processes, should this approach be desirable. It has been found that when applying the radiation curing technique, the exposure time is decreased greater than 5-fold over the epoxy curable resins under the same conditions of duration and intensity. Also, it is found that the present resins are strongly bonded to conventional substrates such as glass, wood, metal, ceramic, plastic and other surfaces Having thus generally described the invention, reference is now had to the accompanying examples which illustrate preferred embodiments but which are not to be construed as limiting to the scope of the invention as more broadly set forth above and in the accompanying examples.

EXAMPLE 1

Hydroxybutyl vinyl ether (1200 g.), the epoxide of a soluble phenol-formaldehyde resin* (150 g.) and potassium hydroxide (0.5 g.) were charged into a 2 liter reaction pot. The mixture was heated for 24 hours at 120° C. and then for 48 hours at 150° C. to complete the reaction. Magnesium silicate was then mixed with 300 g. of the crude reaction mixture at room temperature for 1 hour and the resulting mixture was filtered. Finally, excess hydroxybutyl vinyl ether was stripped off at 90° C. and 0.5 mm Hg to recover the desired vinyl ether product

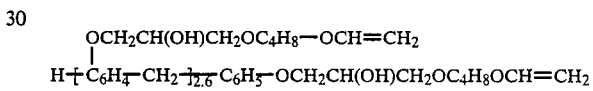

as a gel.
*NOVOLAC DEN-438

EXAMPLE II

Cyclohexane dimethanol (4037.8 g.) and potassium hydroxide (85% pellets, 80 g.) are charged into a 2 gallon stainless steel autoclave. The autoclave was purged three times with nitrogen at 100 psig, heated to 90° C. under 20 mm Hg vacuum for 0.5 hour to remove water. Propane (60 psig) was added and the temperature was raised to 160° C. After the propane pressure was adjusted to 100 psig, acetylene was added to bring the total pressure to 200 psig. The vinylation was discontinued after 4 hours and the crude cyclohexanedimethanol monovinyl ether product was recovered.

The crude product (2633.4 g.) was distilled with a 30-plate Oldershaw column. A center cut of 1711.8 g. was collected at 4 mm Hg between 87° C. and 103° C. The sample contains 57.8% monovinyl ether and 41.8% divinyl ether of cyclohexanedimethanol.

Novolac DEN 438 epoxy resin (40 g.), potassium hydroxide 85% pellets (0.5 g.) and 616 g. of a mixture of 57.8% cyclohexanedimethanol and 41.8% cyclohexanedimethanol were heated at 160° C. in a one liter flask with vigorous stirring for 24 hours. The resulting solution was stirred with 5 g. of magnesium silicate at room temperature for 1 hour and then filtered. The filtrate was concentrated under reduced pressure and the desired multivinyl ether of Novolac DEN 438 epoxy resin was recovered as a gel.

EXAMPLE III

Into a 2 liter reaction pot is charged 180 g. of $HO(CH_2CH_2O)_3CH=CH_2$, 1485 g. of

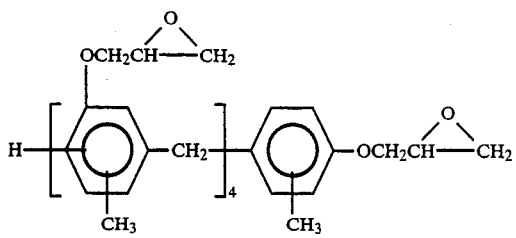

1000 cc of o-xylene and 2 g. of KOH. The mixture is stirred for 1 hour and then heated for 48 hours at reflux temperature. Magnesium silicate (20 g.) is then added and the resulting mixture filtered. The filtrate is then stripped to evaporate xylene under reduced pressure, ∼5 mm Hg, and the product

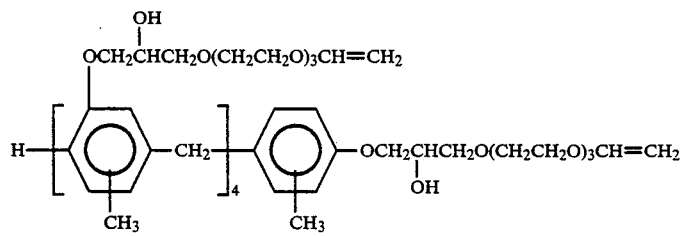

is recovered.

What is claimed is:

1. The benzyloxy vinyl ether having the formula

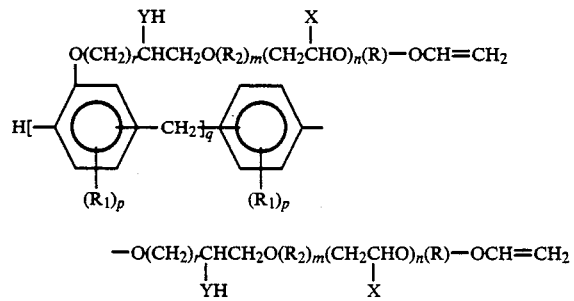

wherein
$R_1$ is lower alkyl;
p is an integer having a value of from 0 to 2;
q is an integer having a value of from 1 to 20;
r is an integer having a value of from 1 to 6;
n is an integer having a value of from 0 to 20;
m is an integer having a value of from 0 to 1;
Y is sulfur or oxygen;
X is hydrogen or methyl and
R and $R_2$ are each independently a radical having from 2 to 20 carbon atoms and are selected from the group of alkylene, arylene, aralkenylene and alkarylene optionally substituted with lower alkyl.

2. The benzyloxy vinyl ether polymer of claim 1 wherein Y is oxygen; n has a value of from 0 to 5; q has a value of from 1 to 5 and r has a value of one.

3. The condensation process which comprises contacting a hydroxy vinyl ether reactant having the formula

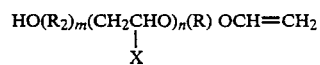

and a poly(benzyloxy) ether co-reactant having the formula

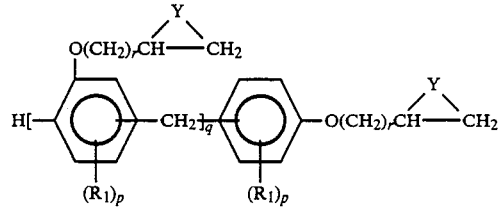

in a mole ratio of between about 1:1 and about 20:1 based on —OH per oxirane or thiirane moiety, and reacting the resulting mixture under anhydrous conditions in the presence of a base catalyst at a temperature of between about 100° C. and about 200° C. to produce the corresponding product of claim 1.

4. The process of claim 3 wherein the mixture is reacted in the presence between about 0.01 and about 10 wt. % based on co-reactant of a metal hydroxide catalyst.

5. The process of claim 4 wherein the concentration of catalyst based on co-reactant is between about 0.1 and about 2 wt. %.

6. The process of claim 5 wherein the mixture is reacted at a temperature of from about 120° to about 175° C.

7. The process of claim 6 wherein the mole ratio of —OH with respect to oxirane or thiirane moiety is in an excess up to about 5 mole %.

* * * * *